(12) United States Patent
Hayes et al.

(10) Patent No.: US 8,466,801 B2
(45) Date of Patent: Jun. 18, 2013

(54) PATIENT MONITORING SYSTEM

(75) Inventors: Stephen Hayes, West Midlands (GB); Stephen Hollyoak, West Midlands (GB)

(73) Assignee: Huntleigh Technology Limited (GB)

( * ) Notice: Subject to any disclaimer, the term of this patent is extended or adjusted under 35 U.S.C. 154(b) by 975 days.

(21) Appl. No.: 12/516,075

(22) PCT Filed: Nov. 28, 2007

(86) PCT No.: PCT/GB2007/004570
§ 371 (c)(1),
(2), (4) Date: Jun. 16, 2009

(87) PCT Pub. No.: WO2008/065402
PCT Pub. Date: Jun. 5, 2008

(65) Prior Publication Data
US 2010/0045474 A1    Feb. 25, 2010

(30) Foreign Application Priority Data

Nov. 29, 2006 (GB) .................................. 0623745.7
Aug. 30, 2007 (GB) .................................. 0716770.3

(51) Int. Cl.
*G08B 21/00* (2006.01)
*G08B 1/00* (2006.01)

(52) U.S. Cl.
USPC ........ 340/666; 340/665; 340/667; 340/573.3; 340/686.1; 340/309.16

(58) Field of Classification Search
None
See application file for complete search history.

(56) References Cited

U.S. PATENT DOCUMENTS

| | | | | |
|---|---|---|---|---|
| 4,994,793 | A * | 2/1991 | Curtis | 340/666 |
| 5,410,297 | A * | 4/1995 | Joseph et al. | 340/573.7 |
| 6,067,019 | A * | 5/2000 | Scott | 340/573.4 |
| 6,583,727 | B2 * | 6/2003 | Nunome | 340/665 |
| 6,819,254 | B2 * | 11/2004 | Riley | 340/665 |
| 2001/0001235 | A1 * | 5/2001 | Menkedick et al. | 340/573.1 |
| 2003/0136201 | A1 | 7/2003 | Hubbard, Jr. | |
| 2006/0028350 | A1 * | 2/2006 | Bhai | 340/666 |

* cited by examiner

*Primary Examiner* — Julie Lieu
(74) *Attorney, Agent, or Firm* — Craig A. Fieschko, Esq.; DeWitt Ross & Stevens S.C.

(57) ABSTRACT

The patient monitoring system comprises at least one load cell element (12) mounted in relation to a support surface, the load cell element (12) determining movement of a person on a support surface. The movement is determined based on a reference (31) measured using the load cell element (12) when the person is positioned on the support surface in a reference position and the subsequent load changes determined using the load cell element in relation to the reference. If the load change exceeds a pre-defined threshold, an alarm (18) is activated. The user is able to set the threshold value of the alarm system according to the physical condition of the patient. For example, in some cases it is necessary to he notified about any movements and in others only major movements are of interest. The patient monitoring system is able to provide a flexible means of monitoring of a patient by a nurse or carer.

20 Claims, 3 Drawing Sheets

PATIENT MONITORING SYSTEM

FIELD OF THE INVENTION

Figure 1:
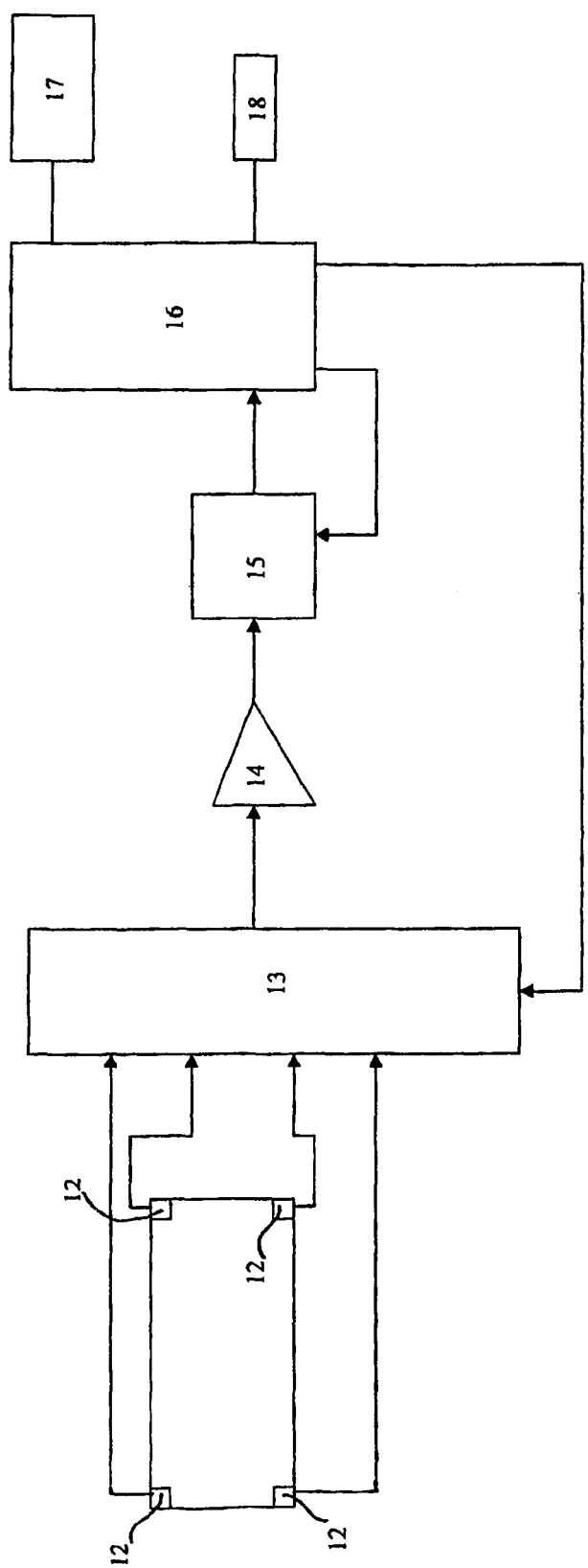

The invention relates to a patient monitoring system by detecting movement of a person on a support surface, for example, a hospital bed.

BACKGROUND OF THE INVENTION

In a hospital where the individual is an injured or ill adult or child or in a nursing home where the individual is an elderly or senile often desirable to know the level of activity of an individual on the bed and to alert the nursing staff that the movements of a patient have reached a level where attention is needed. Providing the nursing staff with such information will improve their efficiency and the quality of the patient care.

One common hospital accident is when a patient climbs out of a hospital bed and is injured either by falling off the bed or by stumbling or falling after successfully getting out of the bed. Essentially the same considerations apply in nursing homes and other similar care facilities. In addition, there are numerous situations at home where it is desirable to know when an invalid, senile person or child is attempting to get out of bed.

SUMMARY OF THE INVENTION

The present invention can assist the nursing staff in their patient care, by providing continuous information on a patient's movement compared to a predetermined pattern of movement, and notify the staff if the movements of the patient exceeds the predetermined pattern.

This predetermined pattern of movement can be a simple function that determines the movement of the patient by comparing a reference value with a fixed range. If the movement by the patient exceeds this range the nursing staff is notified.

Accordingly, the present invention comprises a patient monitoring method by determining movement of a person on a support surface, including at least one load cell element, wherein the movement is determined based on a reference measured using the load cell element when the person is positioned on the support surface in a reference position and the subsequent load changes determined using the load cell element in relation to the reference.

Preferably, the movement is determined when the load changes in relation to the reference exceed a predefined threshold value. In this way, the nursing staff can monitor a patient recovering from a coma or when a patient starts to wake up and therefore starts to move by being notified, preferably by an alarm, when a predefined movement has taken place.

Preferably, the predefined threshold value is adjustable. Therefore, it is possible to adjust the types of movements to be determined and to adjust the sensitivity of an alarm indicating that a predefined movement has taken place. The present invention has the advantage that the carer or nurse can decide the level of movement acceptable for any given patient before they need to intervene.

Preferably, the movement is monitored by determining the load and the monitoring the changes in the load measured by a load cell element.

In a preferred embodiment, the movement is determined as the difference between the load and the load reference.

The differences between the load and the load reference would show the person's movements.

In another aspect, the present invention relates to a computer-readable medium having stored therein instructions for causing a processing unit to execute a method as described above or preferably the method as described above is embedded in a data processing system.

In a preferred embodiment, the invention relates to a movement detection system to be mounted in relation to a support surface for determining movement of a person on the support surface, the system including at least one load cell element to be mounted in relation to the support surface for measuring the load on the support surface, processing means for determining movement based on a relation between a load reference measured using the load cell element when the person is positioned on the support surface in a reference position and the load determined using the load cell element.

Preferably, the load cell element is mounted on a frame supporting the support surface.

Figure 2:
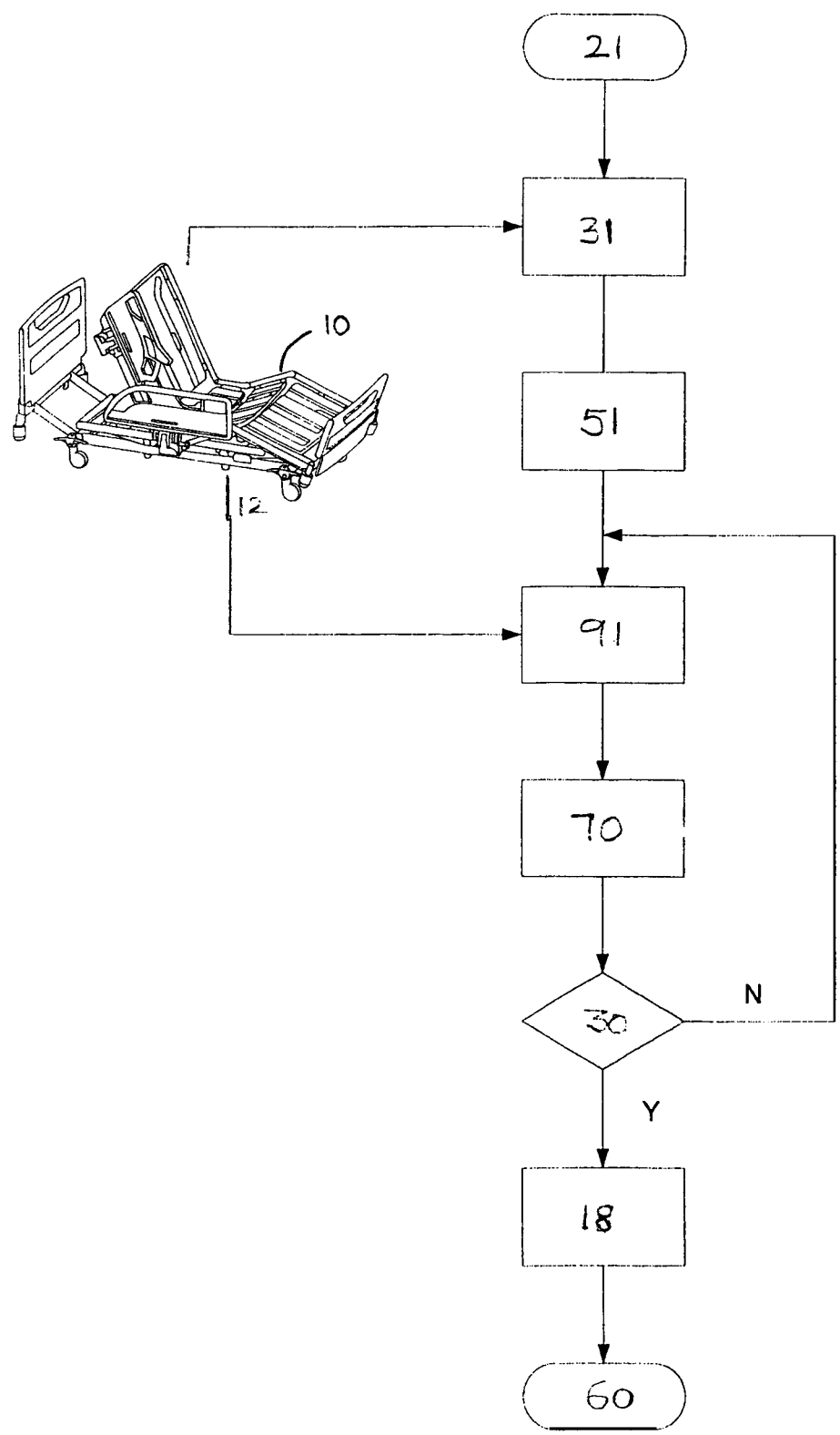
Figure 3A:
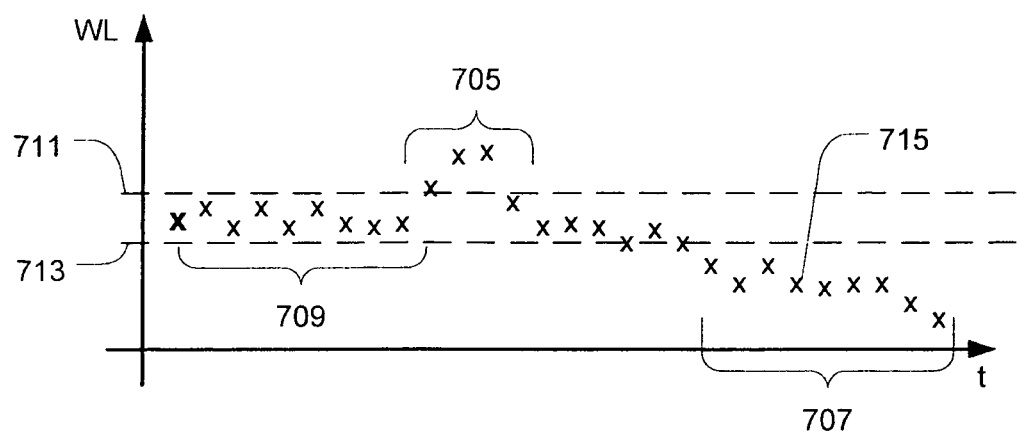
Figure 3B:
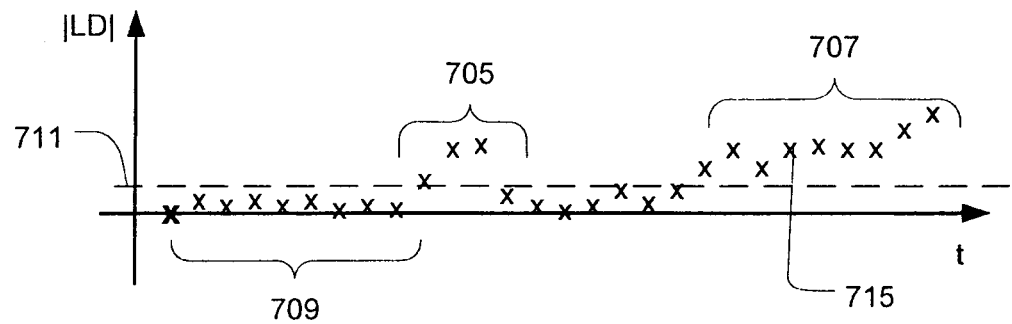

The invention will now be described by way of example and with reference to the figures, where FIG. 1 is a block diagram of a patient monitoring system which embodies the present invention and is incorporated into a hospital bed;

FIG. 2 illustrates a flow diagram of the method of movement detection of a person on a support surface FIGS. 3a and 3b illustrate graphs showing the load on a support surface with a person positioned on the support surface

DETAILED DESCRIPTION OF PREFERRED VERSIONS OF THE INVENTION

Referring to FIG. 1, a hospital bed includes a rectangular patient supporting frame, which is depicted diagrammatically at 10. The frame 10 is itself conventional and not a part of the present invention, and is therefore not described in detail. The frame 10 normally supports a mattress on which a patient rests.

The invention is described with respect to a bed frame 10 supported in a conventional manner by four load cells elements 12 at each corner of the frame 10, the invention is equally applicable to other bed frame and load cell element configurations. Each load cell element 12 produces an electrical signal representative of the weight that it is supporting, including the weight of the frame 10, the mattress and any patient supported on the frame. The total weight of the structure supported by the load cell elements can be obtained by summing the respective weight values measured by the load cell elements. Advantageously, the present invention can use an existing weighing system and at least one of the load cell elements 12 for the patient monitoring system. Therefore an existing weighing system can be further employed as a patient monitoring system. However, the patient monitoring system does not need a weighing system and can be operated as a stand alone system.

FIG. 2 illustrates a flow diagram of the method of patient monitoring according to the invention by determining movement of a person on a support surface such as a support surface on a hospital bed 10 comprising at least one load cell element 12.

The method can be implemented in a computer, and performed using the same microprocessor 16 of the weighing system, if present or otherwise and would in this case start with an initialisation 21, where constants, communication and hardware drivers were initialised.

The method comprises the step of measuring a load reference 31 by using the load cell element 12 when a person is positioned at the bed and is positioned in a reference position. The load reference is obtained by receiving a reference signal from the load cell element measuring the load reference.

Patient monitoring comprising the steps of measuring a current load 91 using the load cell element 12, determining 70 the movement of the person positioned at the hospital bed based on the change between the current load and the stored load reference and based on the determined movement decide 30 whether or not the person positioned in the bed is in danger. This could be that the person has moved when he should not or has moved too much or even is about to leave the bed. The danger point is determined by testing whether or not the difference between the current load and the load reference exceeds a predefined threshold value. If the predefined threshold value is exceeded an alarm/warning 18 is activated, and the monitoring is repeated until the threshold value is exceeded.

The load cell element can be any means suitable for measuring a load on a surface, e.g. piezoelectric sensors or strain gauges or similar. In a preferred embodiment, two load cell elements are spaced at one end of the patient support surface, and the load change on each load cell element is monitored in turn, for a period of one second each. If the load change in either of the load cell elements exceeds the pre-defined threshold, an alarm is activated. The alarm system 18 can use input/output devices, for example a keyboard or control panel 17 to communicate with the monitoring system. The user activates the alarm system via a control panel 17 when movements of a person positioned at the bed need to be monitored.

The user positions the patient in a reference position and as described in FIG. 1 receives a load reference from the load cell element 12. The user is then able to set the threshold value of the alarm system according to the physical condition of the patient. For example, in some cases it is necessary to be notified about any movements and in others only major movements are of interest. Once the alarm system has been activated it will automatically start the monitoring as described in FIG. 1 and if the movement of the patient exceeds the set sensibility level an alarm will start. The alarm 18 could for instance be a loud speaker or a light that alerts the hospital staff. The alarm could be on the support surface as well as remote from the support surface, for example, on a central nurse station.

The patient monitoring system is able to provide a flexible means of monitoring of a patient by a nurse or carer. The nurse or carer can assess the degree of movement acceptable for a given patient and inputs the appropriate threshold value on the control panel 17. In this way, the nurse is able to set any threshold value from a range corresponding to almost no movement of a patient to a patient moving freely around the bed to change their position within the bed and to operate the bed controls, phone, television, the alarm 18 sounding only if the patient leaves the bed. The present invention allows the nurse the flexibility for assessing each patient and setting a level of movement acceptable for that patient before they need to intervene. Depending upon the patient's treatment and health the nurse or carer may want to know when a patient has moved only slightly, or moved parts of the body, or when a patient is turning or shifting up or down the bed or is agitated and climbing within or around the bed to finally exiting the bed.

FIGS. 3a and 3b illustrate graphs showing the asymmetric load L of a support surface with a person positioned on the support surface measured by a load cell element as a function of time t. The graphs illustrate how the load changes as a function of a person's movements on the support surface. The measured load changes when a person positioned at the support surface moves, and the load cell element measures the load asymmetrically.

The first measured load is used as a load reference and the following loads measured illustrate how the load changes due to movements of the person. The load measured increases in the region around 705 which indicates that the person has moved to a position where more load is applied to the load cell element, whereas the load has decreased in region 707. In region 709 the load only changes incrementally about the level of the load reference; which indicates small movements of the person. The movement of a person can be numerical expressed by determining the relation between the load reference and the current load. This can be done by calculating the numerical load difference |LD| by subtracting the load reference from the current load and take the numerical value of the result as illustrated in FIG. 3b. The larger the numerical load difference |LD|, the more movement of the person. Alternatively the load reference can be divided by the current load resulting in a movement index, where an index equal to 1 indicates no movement.

The threshold value can be defined as having an upper limit 711 and a lower 713 limit. If these limits are exceeded an alarm is activated. In the illustrated graph an alarm would be activated in region 705 since these load values exceed the upper limit 711 and in region 707 where the load values exceed the lower limit 713. In order to avoid an alarm activated on the basis of a single load value exceeding the threshold value the method can be adjusted to activate the alarm when a number of successive load values have exceeded the threshold value. In FIG. 3b only an upper limit 711 is defined, as the numerical load difference cannot be less than zero. In region 705 an alarm will not be activated as the number of successive load values exceeding the threshold value is not larger than 3. However in region 707 the alarm will be activated by the load value 715, as this is the fourth successive value that exceeds the lower threshold value.

The movement of the person positioned at a support surface can also be determined by differentiating the graphs illustrated in FIG. 3a or 3b. The differentiated curves can be used to determine the activity of the movements. A large number of zero crossings of the differential curve indicate that the person changes position frequently. Furthermore large differential curves indicate that the person changes position very fast.

The invention claimed is:

1. A method for monitoring patient movement on a support surface including weight sensors, the method including the steps of:
    a. obtaining a reference load measurement from each of the weight sensors when the patient is situated on the support surface in a reference position;
    b. subsequently obtaining current load measurements from each of the weight sensors over time; and
    c. comparing each weight sensor's current load measurement to the weight sensor's reference load measurement,
    wherein a signal is triggered if any weight sensor's current load measurement and the weight sensor's reference load measurement differ by more than a predefined threshold value.

2. The method of claim 1 wherein:
    a. the current load measurements are obtained at regular time intervals; and b. a signal is triggered if several subsequent current load measurements from any of the load cells differ from the reference load measurement by more than a predefined threshold value.

3. The method of claim 2 wherein:
   a. the weight sensors are provided in combination with a threshold control, and
   b. adjustment of the threshold control defines the threshold value.

4. The method of claim 1 further including the steps of:
   a. determining the differences between successive current load measurements from each weight sensor over time; and
   b. triggering a signal if the magnitude of the differences exceeds a predefined magnitude threshold value.

5. The method of claim 1 further including the steps of:
   a. determining the differences between successive current load measurements from each weight sensor over time; and
   b. triggering a signal if the frequency of differences exceeding a predefined magnitude threshold value exceeds a predefined frequency threshold value.

6. The method of claim 1 wherein the current load measurements are obtained at regular time intervals.

7. The method of claim 1 wherein the weight sensors are mounted on a frame supporting the support surface.

8. The method of claim 1 wherein the support surface includes two or more weight sensors spaced apart from each other.

9. The method of claim 1 wherein:
   a. the support surface includes two or more weight sensors, and
   b. the step of obtaining current load measurements over time includes obtaining load measurements from each of the weight sensors in turn.

10. A method for monitoring patient movement on a support surface including weight sensors, the method including the steps of:
    a. situating a patient on the support surface with the patient being in a reference position;
    b. recording a reference load measurement from each of the weight sensors;
    c. setting a threshold value defining a degree of deviation from the reference load measurements;
    d. obtaining current load measurements from each of the weight sensors over time as the patient moves from the reference position; and
    e. triggering a signal if any weight sensor's current load measurement and the weight sensor's reference load measurement differ by more than the threshold value.

11. The method of claim 10 wherein the current load measurements are obtained from each of the weight sensors on a periodic basis.

12. The method of claim 11 wherein the signal is triggered if each of a predefined number of successive current load measurements from one or more of the sensors differs from the reference load measurement by more than the threshold value.

13. The method of claim 11 wherein the signal is triggered if the differences between the current load measurement and the reference load measurement for one or more of the sensors also change over some predefined number of successive current load measurements.

14. The method of claim 1 wherein the signal is triggered if some predefined number of successive current load measurements all differ from each other for one or more of the sensors.

15. The method of claim 11 wherein the signal is triggered if the differences between some predefined number of successive current load measurements are cumulatively greater than a predefined amount.

16. A system for monitoring patient movement on a support surface, the system including:
    a. weight sensors situated on or about the support surface;
    b. a processor:
       (1) obtaining current load measurements from each weight sensor over time;
       (2) comparing each weight sensor's current load measurement to a predefined reference load measurement defined for the weight sensor, the load reference measurement is defined when the patient is situated on the support surface; and
       (3) triggering a signal if any weight sensor's current load measurement and its reference load measurement differ by more than a predefined threshold value.

17. The system of claim 16 wherein the processor repetitively cycles through the weight sensors in turn to:
    (1) obtain the current load measurement from each weight sensor;
    (2) compare the current load measurement from each weight sensor to the predefined reference load measurement; and
    (3) trigger the signal if the current load measurement and the reference load measurement differ by more than a predefined threshold value.

18. The system of claim 17 wherein the weight sensors are spaced about a frame supporting the support surface.

19. The system of claim 16 wherein the signal is triggered if the difference between the current load measurement and the reference load measurement for any of the weight sensors also change over some predefined number of successive current load measurements.

20. The system of claim 16 wherein the signal is triggered if some predefined number of successive current load measurements all differ from each other for any of the weight sensors.

* * * * *